United States Patent [19]

Schmid

[11] Patent Number: 5,117,696
[45] Date of Patent: Jun. 2, 1992

[54] BIAXIAL ACCELEROMETER

[75] Inventor: Felix Schmid, Belfaux, Switzerland

[73] Assignee: Vibro Meter SA, Fribourg, Switzerland

[21] Appl. No.: 669,873

[22] Filed: Mar. 14, 1991

Related U.S. Application Data

[60] Division of Ser. No. 555,671, Jul. 18, 1990, Pat. No. 5,052,226, which is a continuation of Ser. No. 259,244, Oct. 18, 1988, abandoned.

[51] Int. Cl.$^5$ .............................. G01P 15/09
[52] U.S. Cl. .................. 73/517 R; 310/329
[58] Field of Search ............ 73/517 R, 649, 652, 73/654, 517 A; 310/329, 333

[56] References Cited

U.S. PATENT DOCUMENTS

| | | | |
|---|---|---|---|
| 2,808,524 | 10/1957 | Feinstein | 310/329 |
| 3,104,334 | 9/1963 | Bradley, Jr. et al. | 310/329 |
| 3,233,465 | 2/1966 | Tolliver et al. | 73/517 |
| 3,400,284 | 9/1968 | Elazar | 310/329 |
| 3,893,342 | 7/1975 | Florian et al. | 310/329 |
| 4,085,349 | 4/1978 | Farstad | 310/319 |
| 4,144,747 | 3/1979 | Datwyler, Jr. | 310/338 |
| 4,262,544 | 4/1981 | Herzl | 310/338 |
| 4,344,010 | 8/1982 | Vig et al. | 310/361 |
| 4,430,895 | 2/1984 | Colton | 73/497 |
| 4,447,755 | 5/1984 | Ghiurea | 310/329 |
| 4,495,433 | 1/1985 | Sheridan | 310/329 |
| 4,586,377 | 5/1986 | Schmid | 310/329 |
| 4,611,490 | 9/1986 | Takeuchi | 73/505 |
| 4,776,222 | 10/1988 | Lew | 73/862.68 |

FOREIGN PATENT DOCUMENTS

| | | |
|---|---|---|
| 2906451 | 7/1980 | Fed. Rep. of Germany . |
| 836194 | 6/1960 | United Kingdom . |
| 1601547 | 10/1981 | United Kingdom . |
| 2114301 | 8/1983 | United Kingdom . |

Primary Examiner—John E. Chapman
Attorney, Agent, or Firm—Marks & Murase

[57] ABSTRACT

The seismic mass is fixed to the mounting base by a tension bolt. This bolt passes with an important play through an opening of a piezoelectric transducer arranged between the mounting base and the seismic mass. Under the influence of inertial forces which act perpendicularly to the axis of the bolt on the seismic mass, bending loads occur which result in an increase of the pressure at one side and in a decrease of the pressure at the other side of the piezoelectric transducer. The piezoelectric transducer has four electrodes mounted on its top face and four electrodes mounted on its bottom face so as to provide a biaxial accelerometer.

2 Claims, 1 Drawing Sheet

BIAXIAL ACCELEROMETER

This application is a division of Ser. No. 555,671 filed Jul. 18, 1990, now U.S. Pat. No. 5,052,226, which is a continuation of Ser. No. 07/259,244, filed Oct. 18, 1988, abandoned.

BACKGROUND OF THE INVENTION

The present invention relates to an accelerometer with a seismic mass which exerts inertial forces on at least one electromechanical transducer under the influence of accelerations.

Known accelerometers of this kind comprise between a mounting base and the seismic mass of the accelerometer an element sensitive to pressure, preferably a piezoelectric transducer element. These transducer elements are generally in form of flat-shaped disks which are polarized in the same direction as the force to be measured. The surface of the electrodes for deriving the charges produced are perpendicular to the direction of polarization, respectively to the direction of pressure.

Similar accelerometers with transducer elements strained to shear, more particularly piezoelectric elements, are known. In this case, the elements are flat or annular-shaped and they are polarized parallel to the direction of the force to be measured. The surface of the electrodes which derive the charges produced, are oriented in parallel with the direction of polarization, respectively, the direction of shear. In the case of annular elements, the polarization and the direction of the force to be measured is mostly axial.

All known accelerometers use pressure or shear strains which act over the full section of the transducer element. Such transducers are relatively sensitive to external influences, e.g. electric or electromagnetic fields which may induce disturbing signals in the electrodes.

SUMMARY OF THE INVENTION

It is the object of the invention to take measures for reducing such disturbing influences, with the simplest means and high sensitivity of the accelerometer. Embodiments of the invention with their particular advantages will be further described with reference to the drawings.

DETAILED DESCRIPTION OF THE INVENTION

Figure 1:
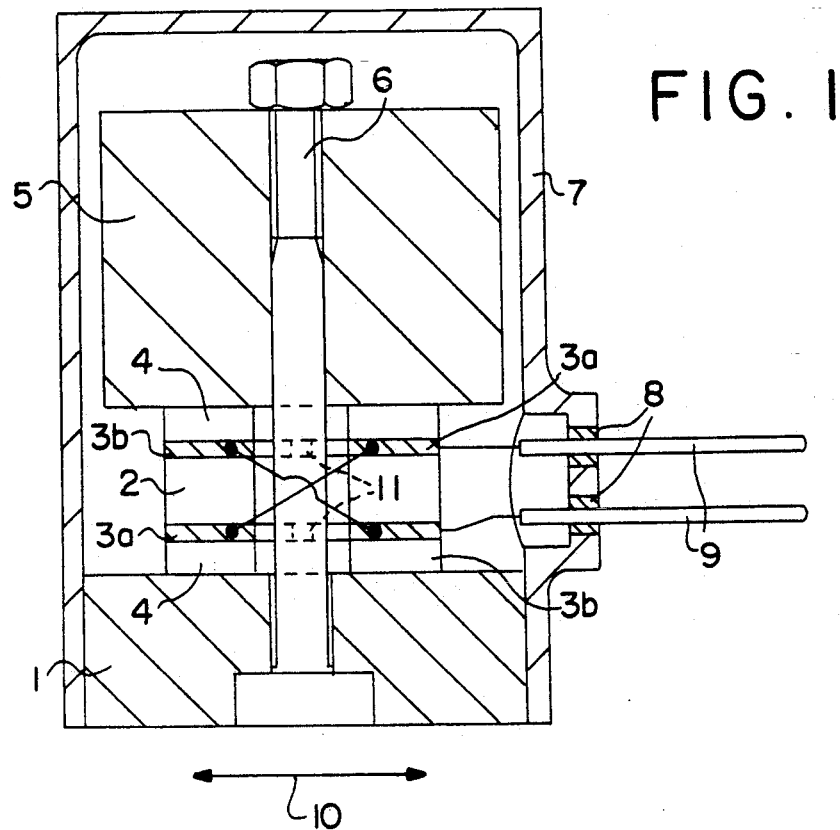
FIG. 1 shows a cross section through the biaxial accelerometer of the present invention.

The accelerometer illustrated in FIG. 1 comprises a mounting base 1 and a piezoelectric transducer element 2 with electrodes x+ and x− (FIG. 2) on each face. The transducer consisting of the transducer element 2 and the electrodes x+, x−, y+, y− comprises on both sides insulation disks 4. The seismic mass 5 is screwed by means of a bolt 6 on to the mounting base 1 and it is pressed against the transducer with such an initial tension that the parts are prestressed and immovably held for all conditions of operation and for each possible orientation of the accelerometer. Through a housing 7, the active mechanical parts are protected and tightly locked. Tight passages 8 for terminal pins 9 are provided in the wall of the housing. As mentioned, both terminal pins 9 are connected with adjacent electrodes x+ and x− which are in turn cross connected with the corresponding central-symetrical electrodes x+ and x− respectively. Fastening holes (not shown) for the assembly of the accelerometer are provided in the mounting base. The arrow 10 in FIG. 1 shows one axis of sensitivity of the accelerometer. If acceleration occurs in this axis of sensitivity, the inertial forces of the seismic mass 5 produce bending stresses which result in opposite variations of the forces of pressure in the left hand side and the right hand side in the transducer parts illustrated in FIG. 1 or FIG. 2. As an example, an increase of the pressure will take place in the right part of the transducer provided with a pair of electrodes x+ and x− and a decrease of the pressure will occur in the left part. In this manner, variations of strains at the pairs of electrodes considered will take place which are directed in opposite directions. In other words, the variations of the pressures and of the strains take place in push-pull. Due to the fact that the electrodes of the right and left halves of the transducer are cross connected, respectively connected in push-pull, the opposite variations of the strains occur in the same direction in both pairs of electrodes at the terminal pins 9 which means that a sum of the charges produced takes place. However, external influences which take place practically in the same way on opposite electrodes are fully or largely compensated by the push-pull arrangement and circuit of each two halve electrodes. This permits the achievement of an important reduction of the disturbing influences without losses of the basic sensitivity of the transducer.

An important novelty with respect to the known embodiments consists however in the use of bending moments instead of using, as known, pure forces of pressure or shear. More particularly in the case of relatively slender constructions of the accelerometer, the gain of charge is more favourable for the same geometrical dimensions than in the usual transducer elements sensitive to shear or pressure, because the bending strains, for an increasing length, increase much more rapidly than the corresponding shear or pressure strains. As can be seen from the preceding, the utilization of bending strains permits in the simplest manner, loading the transducer in push-pull so that a usual transducer element may be provided simply with a particular electrode arrangement for achieving the mentioned advantages. In the case of pure pressure or shear strains, such a solution would not be possible. It is further possible to increase the sensitivity for constant dimensions of the seismic mass in that one reduces the surface of the cross section of the transducer. Indication has already been made regarding the electrical and geometrical symmetry of the transducer and to the advantages which result thereof. One is namely not only independent of external disturbing influences but also undesired charges are compensated, like the ones which occur due to temperature variations because of the pyroelectric effect. Mechanical strains which are produced by the elongation of the mounting base and/or the housing (called basestrain and casestrain effects) become largely ineffective because the elongation present in the mounting base or in the housing have approximately the same effect on both halves of the transducer so that the charges produced compensate mutually.

Figure 2:
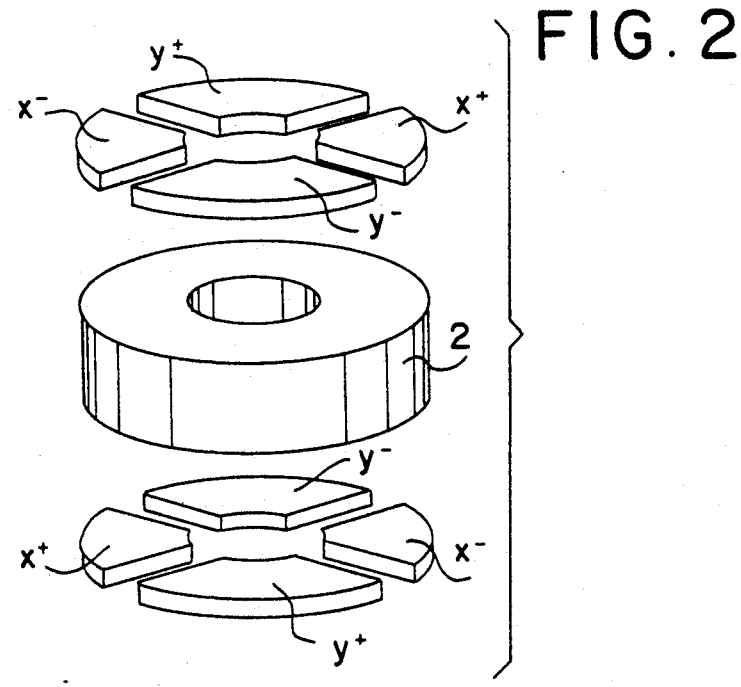
FIG. 2 is an view of an embodiment of the transducer of the present invention.

FIG. 2 shows of a transducer element 2 according to FIGS. 1 which is uniformly polarized in the whole body. However, on this transducer element are not disposed on each side approximately semi-circular-shaped pairs of electrodes but instead four pairs of electrodes, each in form of a circular ring sector of about 90°. For the opposite electrodes of the pairs of the transducer element 2 exist two mutually perpendicular axes of sensitivity correspondingly designated by x+, x−, y+ and y−. The central symmetrical opposite electrodes with the same designation are cross connected together or connected in push-pull and coupled to an output. This results in a biaxial accelerometer for detecting components of accelerations in two directions x, y perpendicular to each other. In this arrangement, the relative difference of sensitivity between both axis depends only on the precision of the geometry of the electrodes when it is assumed that the local repartition of sensitivity within the used piezoelectric disk is constant. This is a significant advantage in comparison with constructions which utilize different transducer elements for each axis because the different elements are mostly of different sensitivities. Piezoelectric accelerometers are adjusted to a determined sensitivity in correspondence to a known techniques, by removing material from the seismic mass. In order to bring both axes to a determined, as far as possible, equal sensitivity to acceleration, the relative difference of sensitivity between both axes must be as small as possible, which is easy to realize in the present case.

Up to now, it was assumed that piezoelectric elements were always used as transducer elements. However, it could also be possible to use corresponding pressure sensitive capacitors with pressure sensitive dielectric, as the case may be also pressure sensitive resistors or inductivities correspondingly connected in push-pull circuit and push-pull arrangement. It is further possible, e.g. in the execution of FIG. 1 to take out all electrodes separately and to connect the terminals to a measuring circuit by means of a switch. In the illuscrated connection, bending moments would be detected in the described manner. On the contrary, if both lower as well as both upper electrodes would be connected together in the usual manner, differences in the pure pressure load, that is components of acceleration in the direction of the axis of the bolt 6 could be detected. For the sake of simplicity there is illustrated always only one transducer element with its electrodes. However, it could be possible to stake in known manner, one upon the other, many disk-shaped transducer elements of the same kind and to connect them correspondingly with the common terminals 9.

As indicated above, the invention is not limited either to the use of bending moments nor to a determined electrode arrangement. Any combinations of all present individual elements may be utilized for advantageous, new arrangements. As an example, a transducer could be provided the ring-shaped transducer element of which is radially polarized. On this transducer element are provided two semi-circular electrodes in accordance with FIG. 2. If such a transducer is loaded perpendicularly to the direction of the gap 11 between the electrodes, that is loaded with shear according to FIG. 1, equal and opposite variations of charges occur in the electrodes as was described previously with respect to FIGS. 1 and 2. By a corresponding push-pull circuit, the same effects are achieved with respect to the compensation of external influences, as in the described and illustrated embodiments.

It is advantageous but not absolutely necessary that transducer elements in one piece comprise parts or zones loaded in opposition. More particularly in FIG. 1, two separate transducer elements could be provided.

I claim:

1. An accelerometer comprising:
    a mounting base, a piezo element transducer mounted on said mounting base and comprising:
    a one piece piezo element having a generally cylindrical configuration having a bottom face, a top face and an axis extending through the center and perpendicular to the top and bottom faces, said piezo element being adapted to be loaded in opposite directions by lateral accelerations,
    four electrodes mounted on the top face and four electrodes mounted on the bottom face of said piezo element so as to provide a biaxial accelerometer,
    means for electrically connecting each top electrode with the symmetrically opposite bottom electrode, and
    output terminals connected to each pair of interconnected electrodes,
    a seismic mass mounted on said transducer,
    means for securing together and prestressing said transducer and said seismic mass against said mounting base, and
    a housing attached to said mounting base and enclosing therein said transducer, said seismic mass and said securing means,
    said seismic mass being displaceable relatively to said mounting base such that influences on said seismic mass act on said piezo element to produce simultaneous but opposite mechanical loading of halves of said piezo element such that electrical signals on differently loaded halves of said piezo element are added to produce output signals at said output terminals responsive to said seismic influences.

2. An accelerometer comprising:
    a mounting base, a piezo element transducer mounted on said mounting base and comprising:
    a one piece piezo element having a disc-shaped configuration having a bottom face, a top face and an axis extending through the center and perpendicular to the top and bottom faces, said piezo element being adapted to be loaded in opposite directions by lateral accelerations,
    four electrodes mounted on the top face and four electrodes mounted on the bottom face of said piezo element so as to provide a biaxial accelerometer,
    means for electrically connecting each top electrode with the symmetrically opposite bottom electrode, and
    output terminals connected to each pair of interconnected electrodes,
    a seismic mass mounted on said transducer at the side opposite said mounting base,
    means for securing together said transducer and said seismic mass on said mounting base, and
    a housing attached to said mounting base and enclosing therein said transducer, said seismic mass and said securing means,
    said seismic mass being displaceable relatively to said mounting base such that influences on said seismic mass act on said piezo element to produce simultaneous but opposite mechanical loading of portions of said piezo element such that electrical signals on differently loaded portions of said piezo element are added to produce output signals at said output terminals responsive to said seismic influences.

* * * * *